United States Patent [19]
Lee

[11] Patent Number: 6,102,660
[45] Date of Patent: Aug. 15, 2000

[54] MINIATURE FAN FOR AIR FRESHENER

[76] Inventor: Pao-Feng Lee, P.O. Box 82-144, Taipei, Taiwan

[21] Appl. No.: 09/290,195

[22] Filed: Apr. 13, 1999

[51] Int. Cl.$^7$ ................................................. B01D 47/00
[52] U.S. Cl. ..................... 416/146 R; 416/55; 416/93 R; 416/244 R; 422/124; 454/155; 454/157
[58] Field of Search ................................. 416/54, 55, 63, 416/93 R, 146 R, 244 R, 246, 247 R; 422/124; 454/155, 156, 157, 328

[56] References Cited

U.S. PATENT DOCUMENTS

| | | | |
|---|---|---|---|
| 5,407,642 | 4/1995 | Lord | 422/122 |
| 5,820,792 | 10/1998 | Lin | 422/124 |
| 5,932,147 | 8/1999 | Chen | 422/124 |

*Primary Examiner*—Edward K. Look
*Assistant Examiner*—Liam McDowell
*Attorney, Agent, or Firm*—A & J

[57] ABSTRACT

A miniature fan for air freshener includes a freely rotatable fan seat, a bearing mounted at the center of the fan seat, a holder at the bottom of the fan seat, a container within the fan seat, a top cap mounted on the top of the container, a fastening nut and a fastening means mounted at the bottom of the holder, characterized in that the fan seat includes central slot, a circular conduit wall, a plurality of inner blades mounted in between the conduit wall and the central slot, and a plurality of rotatable outer blade mounted at the outer surrounding of the circular conduit wall, the bearing is mounted within the central slot and the bottom shaft of the container is pivotally inserted into the shaft hole of the bearing, the protruded top end of the holder is connected to the bottom shaft of the container and is combined together by means of the fastening nut, and a fragrance platelet is mounted within the container having a protruded shaft to adapt to the center hole of the fragrance platelet. By means of the fastening means, the miniature fan is mounted at the air vent of an automobile and the air stream causes the holder to rotate in all direction and the fan seat to rotate soundlessly with the production of fragrance odor within the interior of the automobile.

5 Claims, 8 Drawing Sheets

MINIATURE FAN FOR AIR FRESHENER

BACKGROUND OF THE INVENTION (a) Field of the Invention

The present invention relates to a miniature fan, and in particular, to a miniature fan for air freshener mounted at the air vent of an automobile. The rotation of the fan disperses the fragrance of the air freshener within the interior of the automobile.

(b) Description of the Prior Art

Conventional miniature fan for air freshener normally does not power by motor. The fan rotates by means of air stream and it is usually mounted at the air vent of the automobile to disperse the fragrance of the air freshener.

FIGS. 6 and 7 show a conventional miniature fan having a body 11, a housing 12 mounted to the body 11, a fan 13 within the interior of the body 11, and a fragrance container 14 mounted at the bottom of the interior of the body 11, wherein the rear of the housing 12 has a upper clip 121 and a lower chip 122 to mount the fan at the air vent of the automobile.

FIGS. 7 and 9 show another conventional miniature fan comprising a pair of housings 21, 22 mounted to each other, a fan 23 mounted at the top of the housings 21, 22, a fragrance platelet 24 being contained within the interior of the housings 21, 22 and a cap 25 mounted at the front section of the housing 21, wherein, the rear section of the housing 22 is provided with a slot 221 for its mounting to a wall.

FIGS. 10 and 11 show a further conventional miniature fan comprising a tube body 3 1, a pair of fans 32 mounted at the front section of the tube body 31, and two housing 33 mounted at both ends of the tube body 31, wherein, the rear section of the tube body 31 is provided with a double clips 311, 312 mountable to the air vent of the automobile, and the rear and front wall of the tube body 31 are provided with an air inlet 313 and an air outlet 314.

The drawbacks of these conventional miniature fans for air refresher are as follows:

(1) The fan is mounted at the air vent and the direction of air stream is fixed, i.e., only a specific direction of air stream is provided.
(2) The size of the miniature fan is relatively large which occupies a larger space and blocks the direction of air stream.
(3) The ornamental design does not have an aesthetic appearance.
(4) The blades of the fan are mounted to a rotating shaft and there is a frictional resistance between the shaft hole of the housing and the rotating shaft. Thus, the speed of rotation is restricted.

SUMMARY OF THE PRESENT INVENTION

The present invention relates to a miniature fan, and in particular, to a miniature fan for air freshener mounted at the air vent of an automobile.

It is an object of the present invention to provide a miniature fan for air freshener comprising a miniature fan for air freshener comprising a freely rotatable fan seat, a bearing mounted at the center of the fan seat, a holder at the bottom of the fan seat, a container within the fan seat, a top cap mounted on the top of the container, a fastening nut and a fastening means mounted at the bottom of the holder, characterized in that the fan seat includes a central slot, a circular conduit wall, a plurality of inner blades mounted in between the conduit wall and the central slot, and a plurality of rotatable outer blade mounted at the outer surrounding of the circular conduit wall, the bearing is mounted within the central slot and the bottom shaft of the container is pivotally inserted into the shaft hole of the bearing, the protruded top end of the holder is connected to the bottom shaft of the container and is combined together by means of the fastening nut, and the bottom of the holder is provided with a ball hole which is engageable with the shaft ball at the top end of the fastening means, a fragrance platelet is mounted within the container having a protruded shaft to adapt to the center hole of the fragrance platelet so as to position the fragrance platelet, and the top cap covers the container; by means of the fastening means, the miniature fan is mounted at the air vent of an automobile and the air stream causes the holder to rotate in all direction and the fan seat to rotate quietly with the production of fragrance odor within the interior of the automobile.

It is another object of the present invention to provide a miniature fan for air refresher which allows the dispersion of fragrance odor within the interior of the automobile.

It is yet another object of the present invention to provide a miniature fan for air refresher, wherein the rotation of the fan is quiet.

It is another object of the present invention to provide a miniature fan for air refresher, wherein the fan can be easily mounted or dismantled at any surrounding, such as a standing fan or an air-conditioner.

It is another object of the present invention to provide a miniature fan for air refresher, wherein the fan does not need any external power in order to drive the fan.

Additional advantages of this invention will become apparent from the description which follows, taken in conjunction with the accompanying drawings.

DETAILED DESCRIPTION OF THE PREFERRED EMBODIMENT

Figure 1:
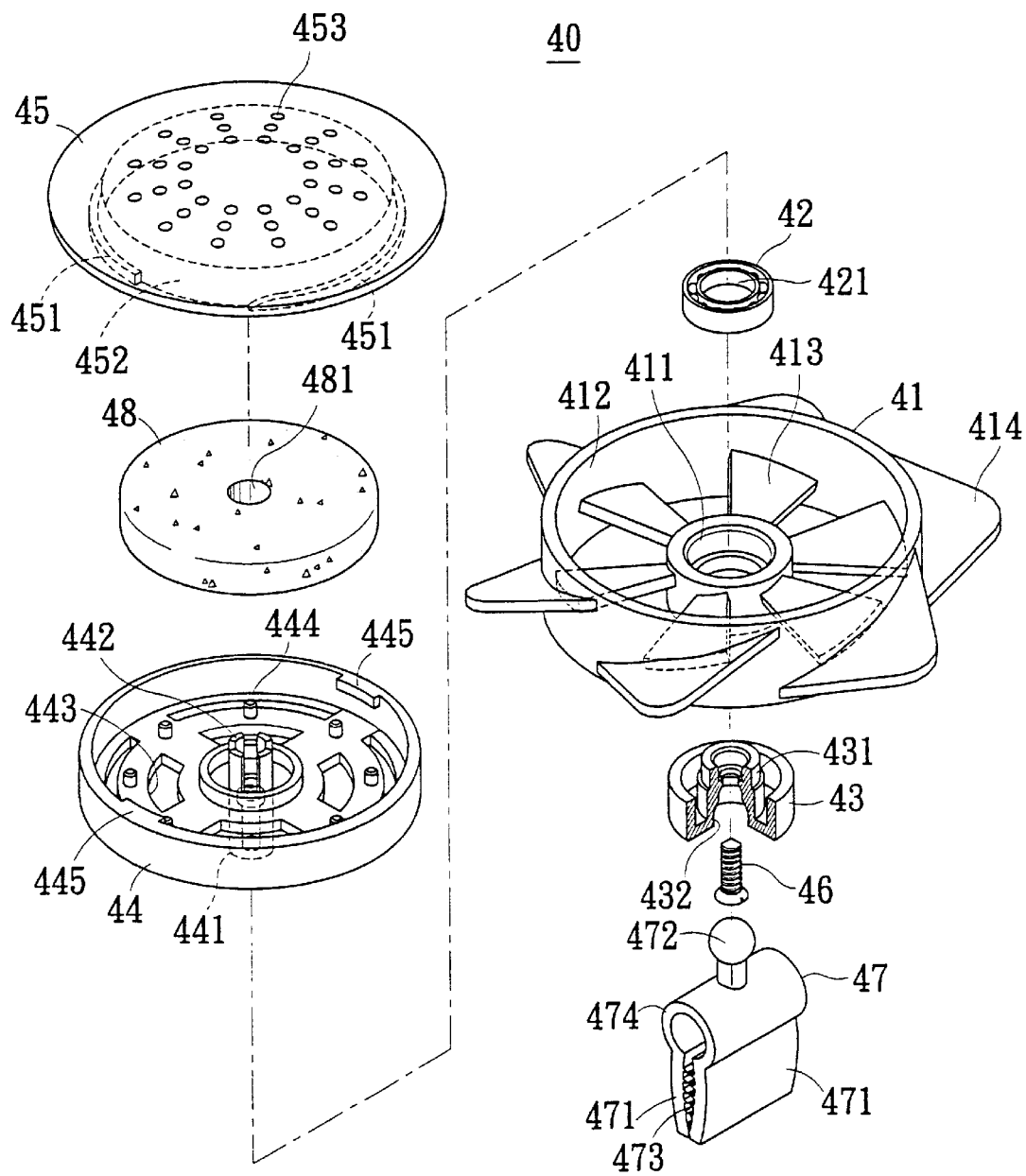
FIG. 1 is a perspective exploded view of a miniature fan for air freshener in accordance with the present invention.
Figure 2:
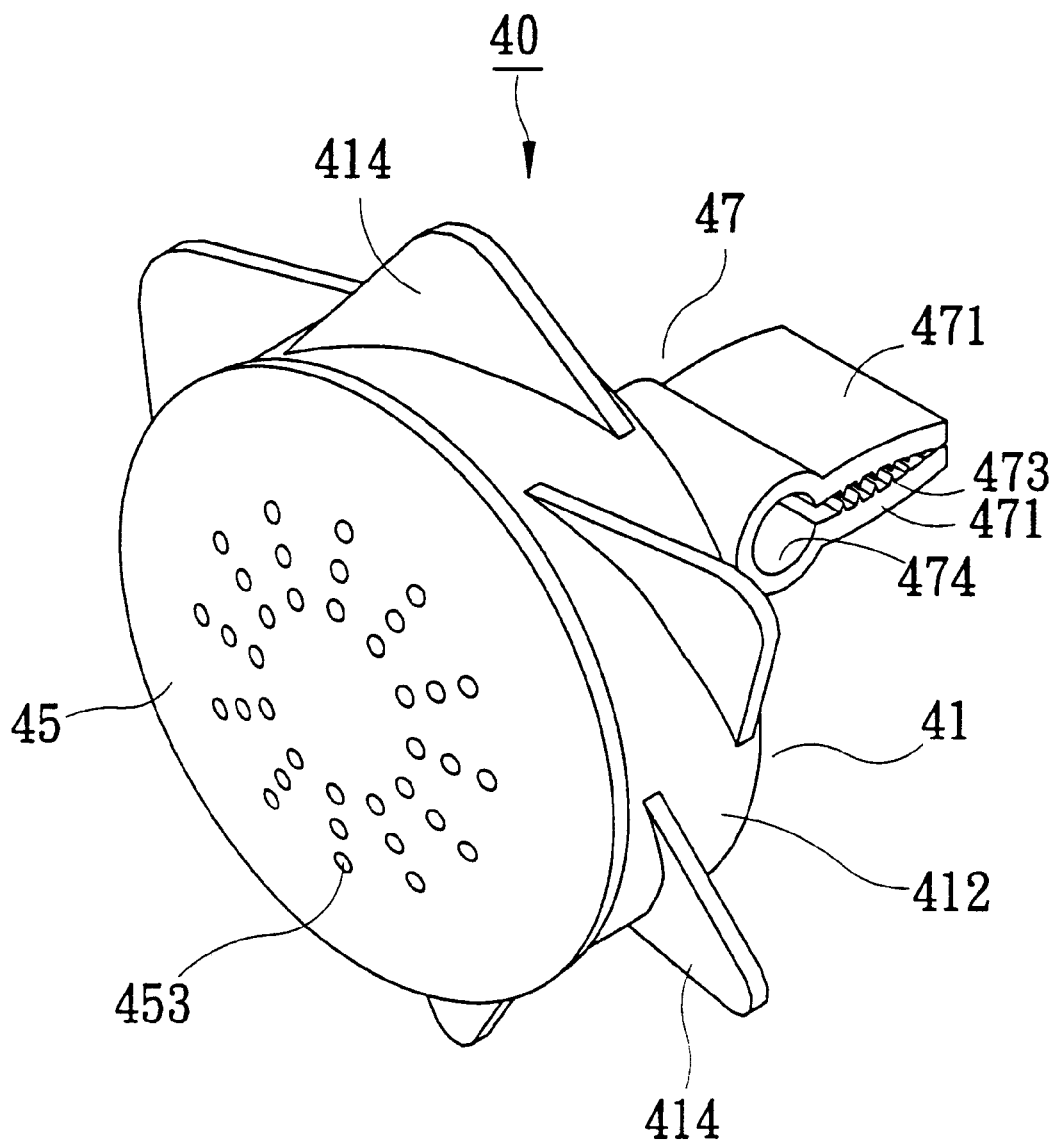
FIG. 2 is a perspective view of a miniature fan for air freshener in accordance with the present invention.

FIG. 1 is a perspective exploded view of the miniature fan for air freshener in accordance with the present invention and is designated with reference numeral 40. The miniature fan 40 comprises a freely rotatable fan seat 41, a bearing 42 mounted at the center of the fan seat 41, a holder 43 at the bottom of the fan seat 41, a container 44 within the fan seat 41, a top cap 45 mounted on the top of the container 44, a fastening nut 46 and a fastening means 47 provided to the bottom of the holder 43. The combination of all the parts form a structure shown in FIG. 2.

Figure 3:
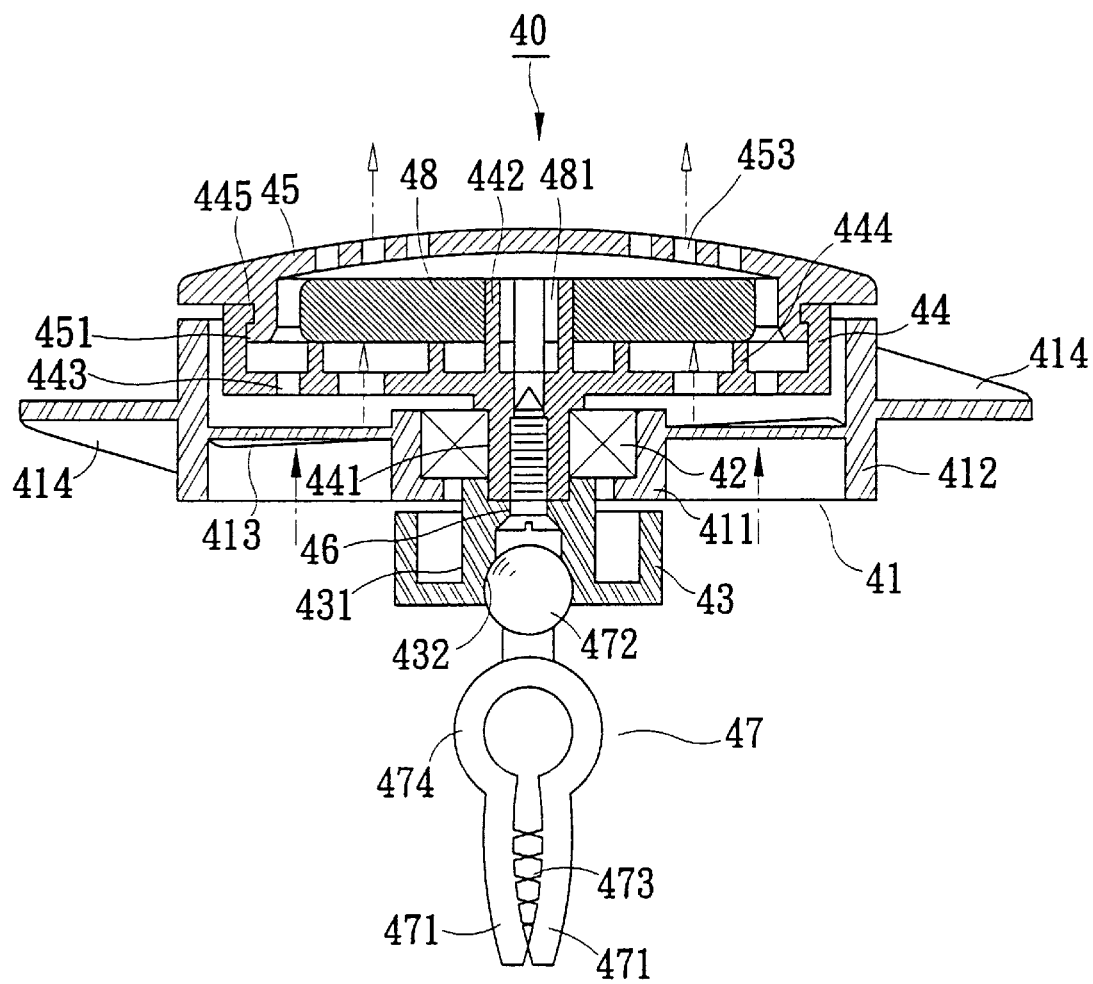
FIG. 3 is a sectional view of a miniature fan for air freshener in accordance with the present invention.

Referring to FIGS. 1 and 3, the fan seat 41 includes a central slot 411, a circular conduit wall 412, a plurality of inner blades 413 mounted in between the conduit wall 412 and the central slot 411, and a rotatable outer blade 414 mounted at the outer surrounding of the circular conduit wall 412. In the central slot 411, a bearing 42 is provided, and the shaft hole 421 of the bearing 42 is pivotally disposed with the bottom shaft 441 of the container 44.

In accordance with the present invention, the top end of the protruded tube 431 of the holder 43 is connected to the bottom shaft 441 of the container 44 (refer to FIG. 3), and by means of the fastening nut 46, the holder 43 is secured to the container 44.

In the present invention, the center of the interior of the container 44 is provided with a protruded shaft 442 which is insertable with the center hole 481 of the fragrance platelet 48 so that the fragrance platelet 48 is positioned The bottom surface of the container 44 is provided with a plurality of holes 443 to allow air stream to enter. In addition, the bottom surface of the container 44 is provided with a plurality of protrusions 444 to support the fragrance platelet 48 such that a distance is provided in between the fragrance platelet 48 and the bottom surface of the container 44. This distance allows air to flow from the container 44 to the surroundings. In accordance with the present invention, the fragrance platelet 48 can be replaced with a plurality of fragrance beads (not shown).

Referring again to FIG. 1, the top edge of the container 44 is provided with a pair of stopping blocks 445 and the bottom edge of the top cap 45 is provided with two arc-shaped protruded rims 451. A recess 452 is formed between the rims 451. The recess 452 allows the stopping blocks 445 to rotate along the protruded rims 451, and the top cap 45 can be positioned at the container 44. In addition, a plurality of air vents 453 are provided on the surface of top cap 45 so that the fragrance of the fragrance platelet 48 can disperse via these vents 453.

Figure 4:
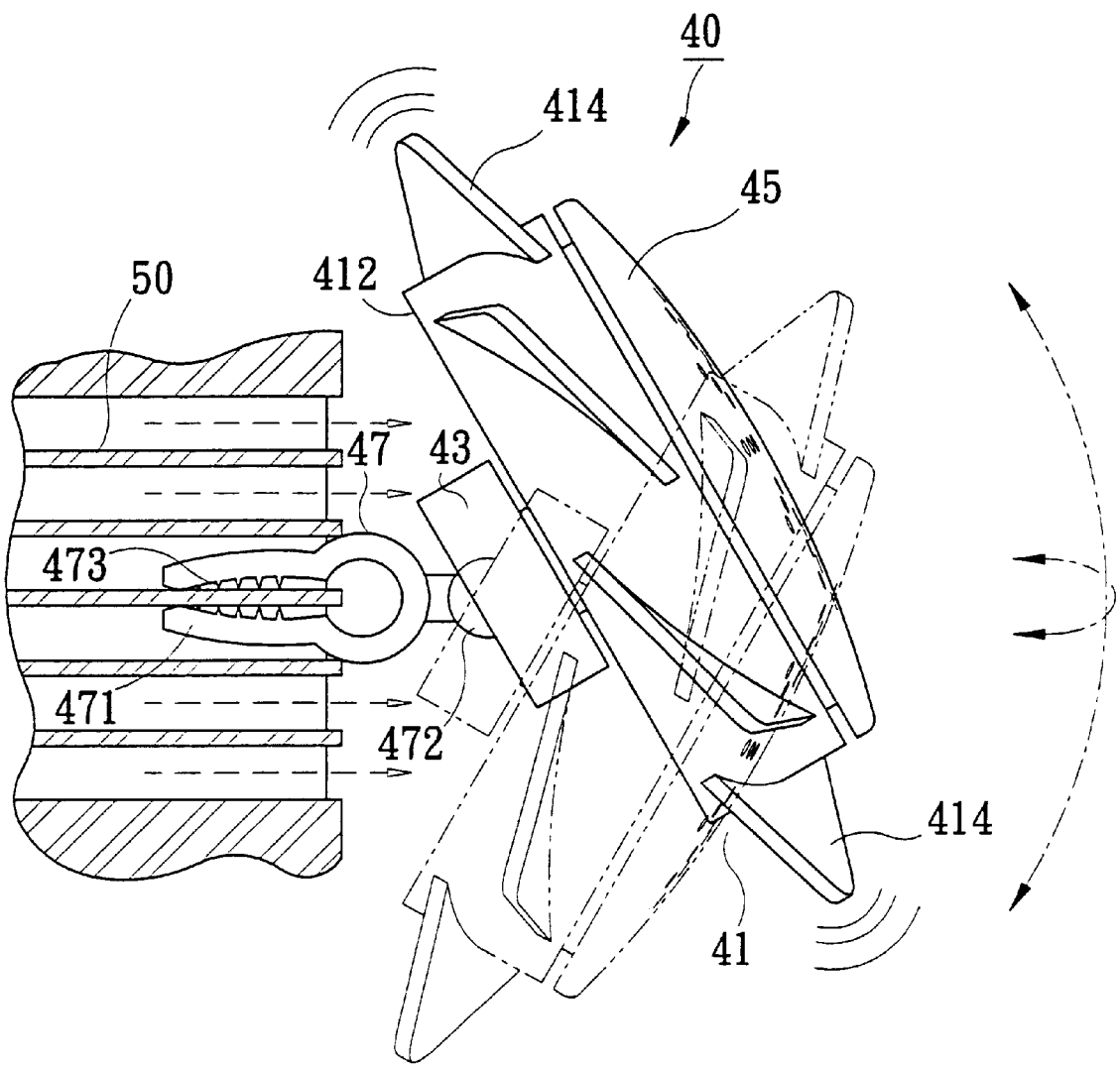
FIG. 4 is a preferred embodiment of a miniature fan for air freshener in accordance with the present invention.

Referring to FIG. 4, the miniature fan 40 is mounted to the air vent 50 of the automobile by means of a fastening means 47 with double clips 471. The fastening means 47 has an opened circular tube 474 with two clips 471, and a shafted ball 472 made from plastic materials. The double clip 471 is elastic and its inner surface is provided with a plurality of gripping elements 473 to avoid slippage. In addition, the shafted ball 472 is mountable into the ball hole 432 of the holder 43 such that the holder 43 is rotatable at all angles with the shafted ball 472 as the center. When a stream of air passes the fan seat 41, the inner blades 413 rotate and the outer blades 414 disperse the fragrance odor such that the interior of the automobile has a fragrant smell.

Figure 5:
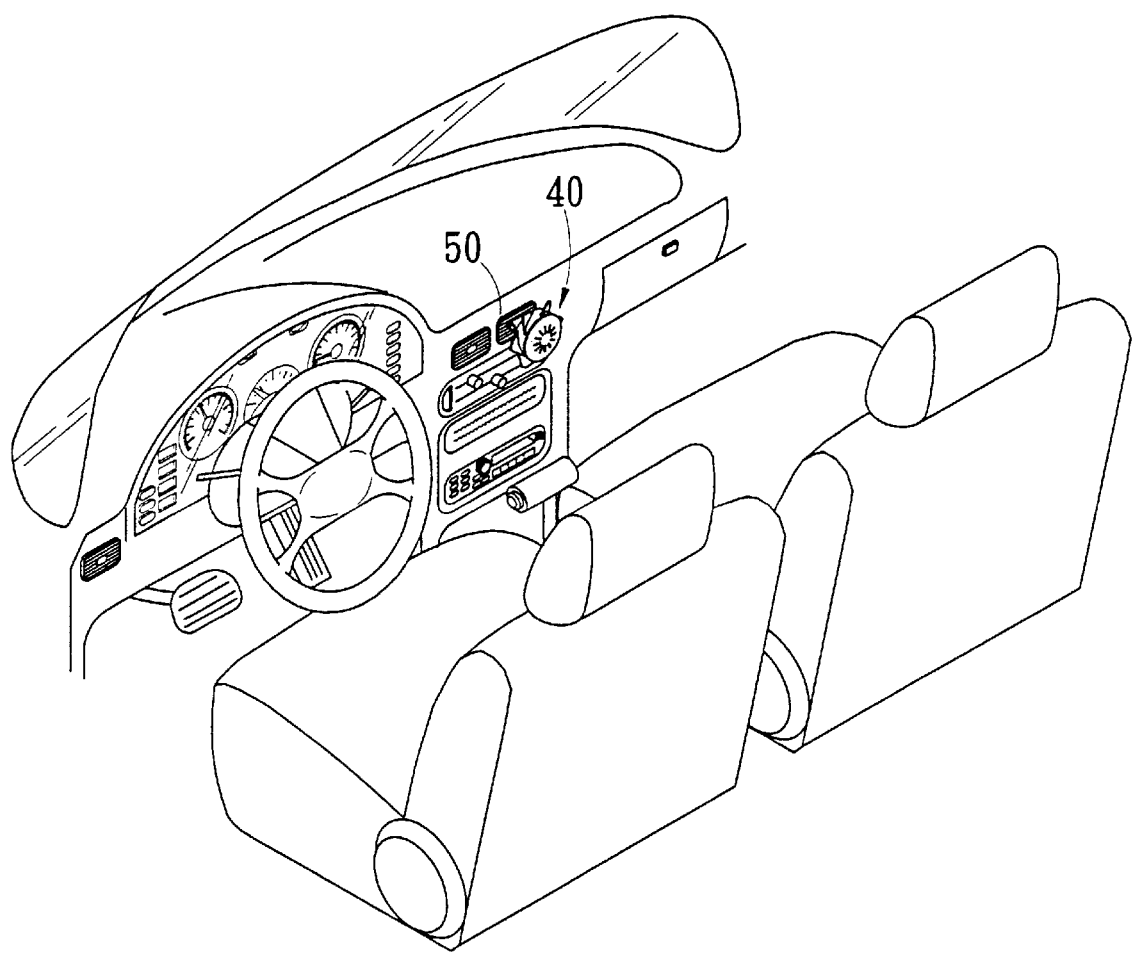
FIG. 5 is a schematic view of a miniature fan for air freshener in accordance with the present invention.
Figure 6:
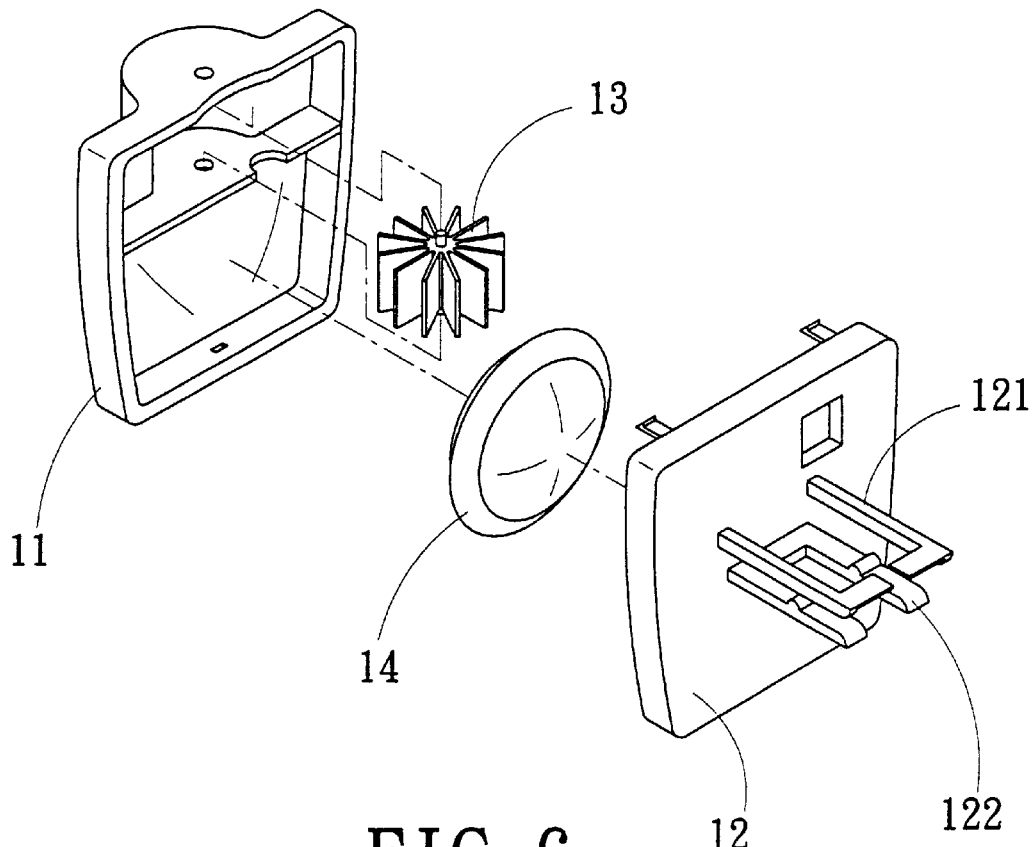
FIG. 6 is an exploded view of a conventional miniature fan for air freshener.
Figure 7:
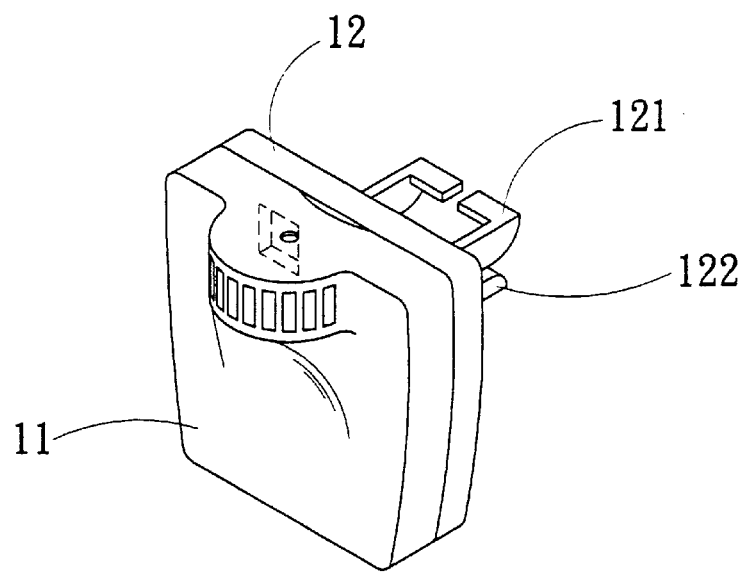
FIG. 7 is a perspective view of a conventional miniature fan for air freshener.
Figure 8:
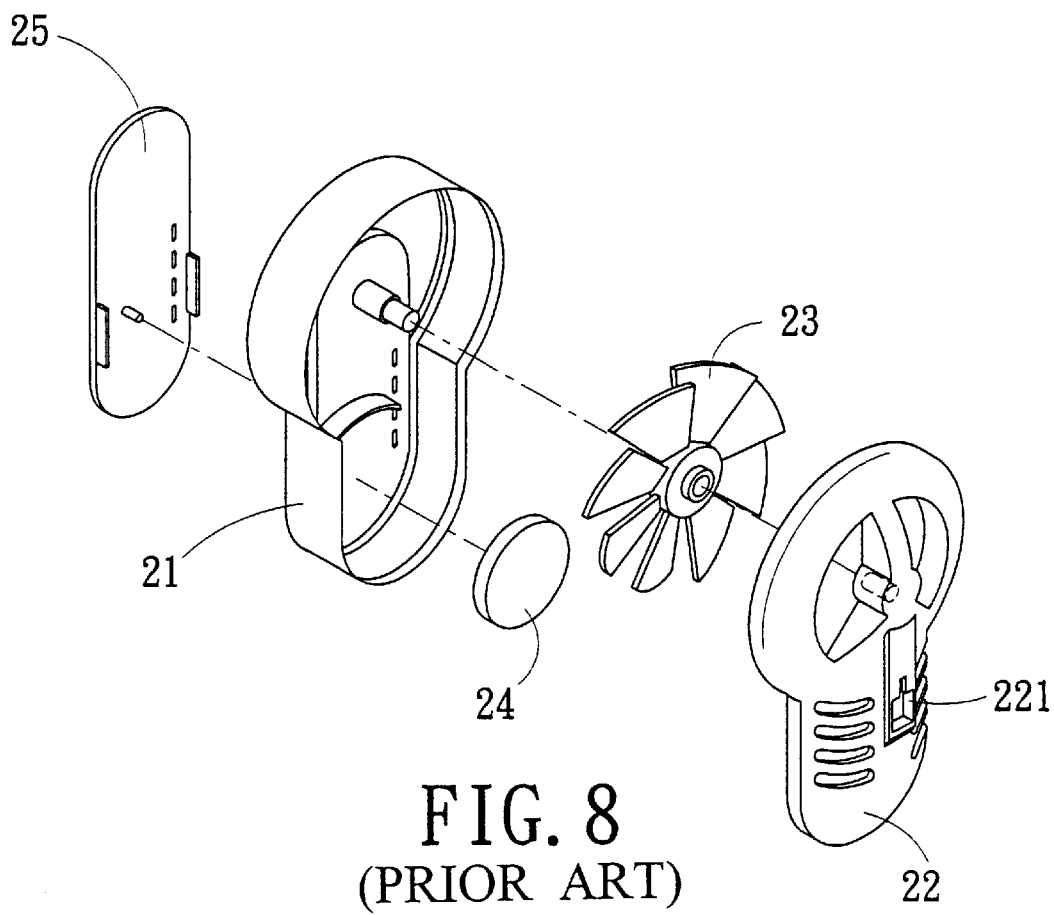
FIG. 8 is an exploded view of a second conventional miniature fan for air freshener.
Figure 9:
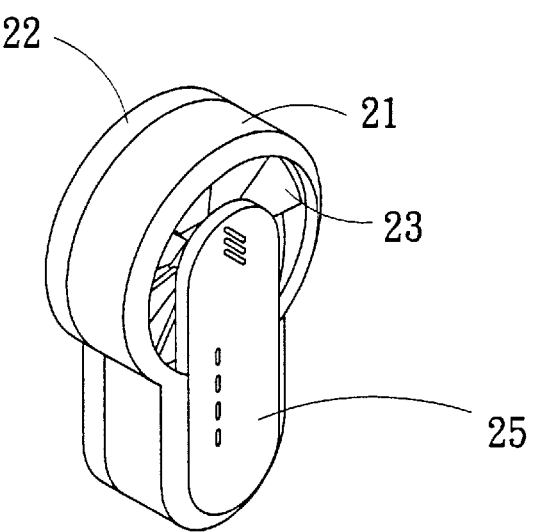
FIG. 9 is a perspective view of a second conventional miniature fan for air freshener.
Figure 10:
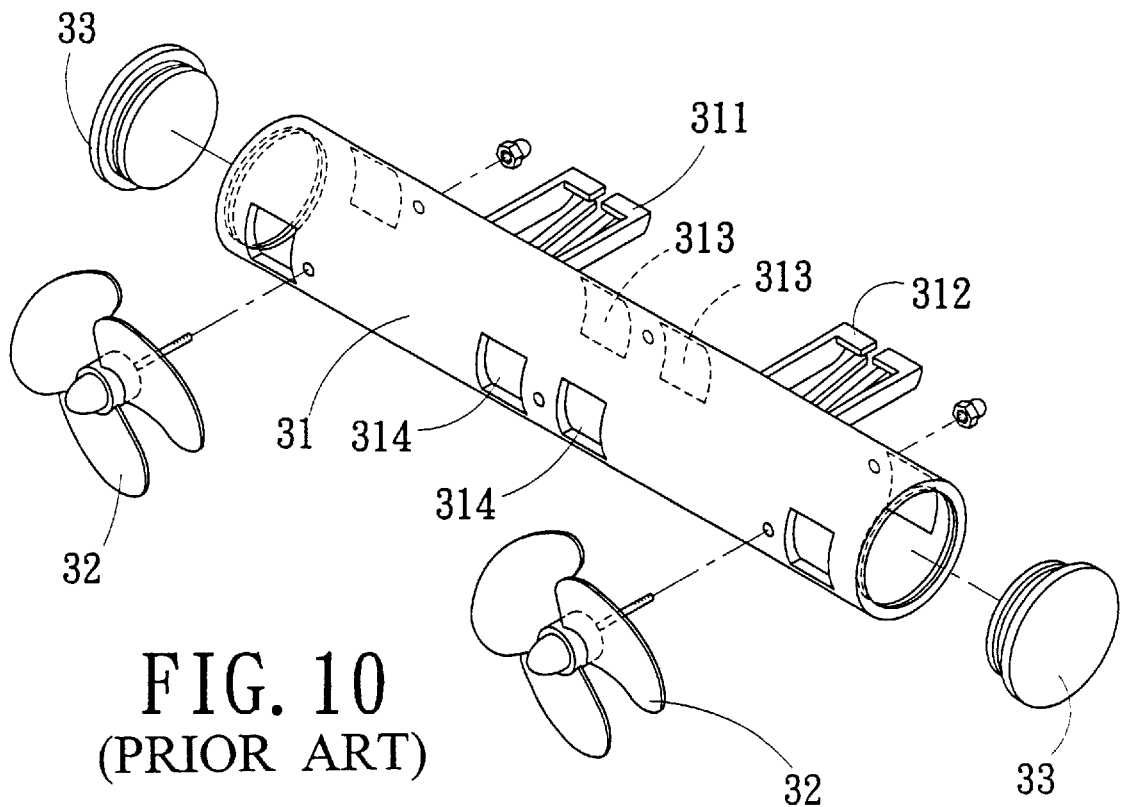
FIG. 10 is an exploded perspective view of a third conventional miniature fan for air freshener.
Figure 11:
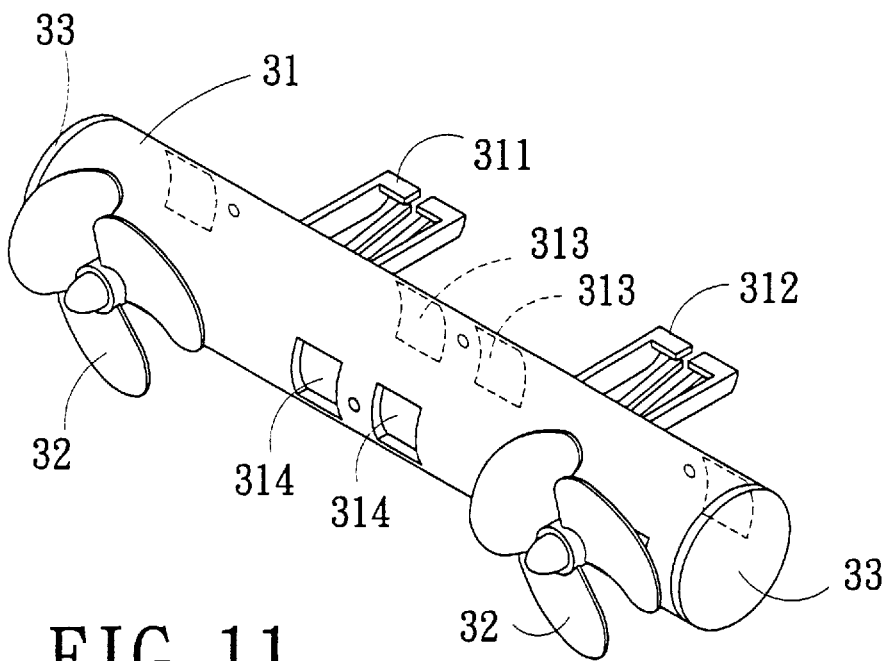
FIG. 11 is a perspective view of a third conventional miniature fan for air freshener.

Referring to FIG. 5, there is shown the mounting of the miniature fan 40 at the air vent 50 of the automobile. In the preferred embodiment, the miniature fan 40 does not need electrical power to drive the blades, and it does not occupy a large space. In accordance with the present invention, it can be mounted at commonly available fan, air-conditioner, heater, etc. Without using electrical power, the miniature fan 40 can be operated to provide fragrance smell to the surrounding.

While the invention has been disclosed and described with specified preferred embodiments, it will be apparent that variations and modification may be made therein, and it is therefore intended in the flowing claims to cover each such variation and modification as falls within the scope and the true spirit of the invention.

I claim:

1. A miniature fan for air freshener comprising a freely rotatable fan seat; a bearing mounted at the center of the fan seat; a holder at the bottom of the fan seat; a container within the fan seat; a top cap mounted on the top of the container; a fastening nut and a fastening means mounted at the bottom of the holder, characterized in that the fan seat includes a central slot, a circular conduit wall, a plurality of inner blades mounted in between the conduit wall and the central slot, and a plurality of rotatable outer blade mounted at the outer surrounding of the circular conduit wall, the bearing is mounted within the central slot and the bottom shaft of the container is pivotally inserted into the shaft hole of the bearing, the protruded top end of the holder is connected to the bottom shaft of the container and is combined together by means of the fastening nut, and the bottom of the holder is provided with a ball hole which is engageable with the shaft ball at the top end of the fastening means; a fragrance platelet is mounted within a container, the container having a protruded shaft to adapt to the center hole of the fragrance platelet so as to position the fragrance platelet and wherein the top cap covers the container; by means of the fastening means, the miniature fan is mounted at the air vent of an automobile and the air stream causes the holder to rotate in all directions and the fan seat to rotate soundlessly with the production of fragrant odor within the interior of the automobile.

2. The miniature fan for air fresher as set forth in claim 1, wherein the container contains a plurality of fragrance beads.

3. The miniature fan for air fresher as set forth in claim 1, wherein the fastener comprises an opened circular tube with a pair of clips, and a plastic shaft ball; a plurality of gripping elements is provided at the inner surface of the clips, and the shaft ball is insertable into the ball hole at the bottom of the holder.

4. The miniature fan for air fresher as set forth in claim 1, wherein a plurality of holes are provided at the bottom surface of the container to allow air stream to enter, and a plurality of protrusions are provided on the bottom surface of the container to support the fragrance platelet such that a distance is provided in between the fragrance platelet and the bottom surface of the container.

5. The miniature fan for air fresher as set forth in claim 1, wherein a plurality of vent holes are provided on the top cap to lead the fragrance odor from the container.

* * * * *